(12) United States Patent
Wellnitz et al.

(10) Patent No.: US 7,304,307 B2
(45) Date of Patent: Dec. 4, 2007

(54) PMT SIGNAL CORRELATION FILTER

(75) Inventors: Donald R. Wellnitz, Fitchburg, WI (US); Michael J. Geagan, Wayne, PA (US); Steven R. Martin, Thorofare, NJ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 84 days.

(21) Appl. No.: 10/561,983

(22) PCT Filed: Jun. 1, 2004

(86) PCT No.: PCT/IB2004/001936

§ 371 (c)(1),
(2), (4) Date: Dec. 21, 2005

(87) PCT Pub. No.: WO2005/000120

PCT Pub. Date: Jan. 6, 2005

(65) Prior Publication Data

US 2006/0151707 A1     Jul. 13, 2006

Related U.S. Application Data

(60) Provisional application No. 60/483,523, filed on Jun. 27, 2003.

(51) Int. Cl.
*G01T 1/20* (2006.01)
*G01J 1/42* (2006.01)

(52) U.S. Cl. ..................... 250/369; 250/395
(58) Field of Classification Search ............... 250/369, 250/395

See application file for complete search history.

(56) References Cited

U.S. PATENT DOCUMENTS

| 4,580,055 A | | 4/1986 | Barfod ................. 250/366 |
| 5,285,072 A | * | 2/1994 | Klingenbeck-Regn et al. ... 250/369 |
| 5,347,129 A | * | 9/1994 | Miller et al. ............. 250/336.1 |
| 5,434,414 A | | 7/1995 | Berlad et al. ........ 350/363.07 |
| 5,508,524 A | | 4/1996 | Goldberg et al. ........... 250/369 |
| 5,793,045 A | | 8/1998 | DiFilippo et al. ...... 250/360.03 |
| 6,329,651 B1 | | 12/2001 | Mestais et al. ........... 250/252.1 |

\* cited by examiner

*Primary Examiner*—David Porta
*Assistant Examiner*—Mindy Vu (57) ABSTRACT

A method of generating a filter (40) for a nuclear medicine system (20) where the filter selects valid detected radiation events for image processing. A dataset (60) is provided that is indicative of a plurality of emitted radiation events occurring over a predetermined period of time. Signals representative of the response of a detector to the dataset of the plurality of emitted radiation events are generated. A pattern is determined (66) based on a correlation of a plurality of signals resulting from the response of the detector to a plurality of single radiation events in the dataset. A filter is generated (74) based on the correlation pattern. A method and apparatus of using the generated filter is also disclosed.

24 Claims, 6 Drawing Sheets

| PMT 1 and 4 Values | PMT 2 and 5 Values | PMT 3 and 6 Values | Number of Occurances |
|---|---|---|---|
| 0 | 0 | 0 | $H_{0,0,0}$ |
| 0 | 0 | | |
| 0 | 0 | | |
| 0 | 0 | | |
| 0 | 0 | Max P | $H_{0,0,Max\,P}$ |
| 0 | | | |
| 0 | | | |
| 0.2 | 0.2 | 0.1 | 1 |
| 0 | Max P | 0 | $H_{0,Max\,P,0}$ |
| 0 | Max P | | |
| 0 | Max P | | |
| 0 | Max P | | |
| 0 | Max P | Max P | $H_{0,Max\,P,Max\,P}$ |
| | | | |
| | | | |
| | | | |
| Max P | 0 | 0 | $H_{Max\,P,0,0}$ |
| Max P | 0 | | |
| Max P | 0 | | |
| Max P | 0 | | |
| Max P | 0 | Max P | $H_{Max\,P,0,Max\,P}$ |
| Max P | | | |
| Max P | | | |
| Max P | | | |
| Max P | Max P | 0 | $H_{Max\,P,Max\,P,0}$ |
| Max P | Max P | | |
| Max P | Max P | | |
| Max P | Max P | | |
| Max P | Max P | Max P | $H_{Max\,P,Max\,P,Max\,P}$ |

110 (points to 0.2, 0.2, 0.1 row)

MATCH TO FIG. 4B

PMT SIGNAL CORRELATION FILTER

CROSS REFERENCE TO RELATED APPLICATIONS

This application claims the benefit of U.S. provisional application Ser. No. 60/483,523 filed Jun. 27, 2003, which is incorporated herein by reference.

The present invention relates to the art of nuclear medical diagnostic imaging and is particularly related to a method and apparatus for selection of desired detected radiation events to be processed for generation of diagnostic images. The present invention is applicable in connection with emission computed tomography including positron emission tomography ("PET") and single photon emission computed tomography ("SPECT") and will be described with particular reference thereto. It is to be appreciated that the present invention is applicable to other nuclear imaging techniques such as planar positron emission/transmission or single photon emission/transmission based imaging.

Diagnostic nuclear imaging is directed to qualitative and quantitative examination of a distribution of radiotracers injected into the subject of the examination, e.g., a patient or test animal. Nuclear imaging systems usually have one or more radiation detectors or gamma cameras. The detectors are mounted in a stationary array around the examining region or are mounted on a movable gantry to view the examination region in which the subject is received for the imaging procedure. Typically, one or more radionuclides or radiopharmaceuticals that generate detectable radiation are introduced into the subject. The radiopharmaceuticals travel to an organ or organs of interest from which the image is to be produced showing the desired physiological activity. The detectors scan the subject along a selected path or scanning trajectory and radiation events emitted from the affected area of the patient are detected.

Typically, a detector includes a scintillator comprising a large scintillation crystal or matrix of smaller scintillation crystals. In either case, the scintillator emits light or another signal indicative of detection of a radiation event. When light is emitted by the scintillator it is detected by a matrix of sensors in optic communication with the scintillator. A commonly employed sensor for use with light emitting scintillators is a photomultiplier tube ("PMT"). The PMTs generate a signal indicative of the energy of the light generated. For a solid state detector maitrix, e.g. CZT elements, detected radiation events result in generation of an electrical signal indicative the detected event. The relative outputs of the PMTs, or solid state detectors, are suitably amplified and processed to generate a signal indicative of the position (X,Y) and energy (E) of detected radiation events. The data is then reconstructed into an image representation of a region of interest.

A conventional method for event positioning is known as the Anger method, which sums and weights signals output by PMTs after the occurrence of an event. More specifically, the energy is typically measured as the sum of all the PMT signals, and the position is typically measured as the "center of mass" or centroid of all the PMT signals.

Generally, a scintillation light flash is mostly contained within a small subset of the PMTs. For example, out of a total number of PMTs, typically on the order of 50 or 60, over 90% of a total signal is detected in the seven (7) PMTs closest to a scintillation flash. However, the centroid calculation can be affected by light from the scintillator undesirably straying to more remote PMTs, or other solid state detectors, noise in the PMT outputs, and the like. In addition, various forms of scattering cause scintillations that do not contribute to the true radiation event that is useful for generating an image. Accordingly, these signals may give rise to an artificial shifting of event location measurements. Stray signals also tend to arise at high-counting rates due to events occurring nearly simultaneously in the scintillator. When two events occur substantially simultaneously, their "center-of-mass" is midway between the two—where no event actually occurred. Again, events can be mispositioned as a result. The precision of the image is related to the accuracy of the determination of location and energy of the detected event.

In present systems, the stray or otherwise undesirable signals (i.e., those not bearing a readily ascertainable relationship to an actual event and/or its true location) are typically characterized by lower PMT signal amplitudes as compared to PMT signals associated with and/or corresponding to actual observed events. Current methods for filtering out events that cannot be properly positioned (i.e. contaminated events) take two general forms, pulse shape analysis and energy analysis. In pulse shape analysis the preintegration scintillation pulse is analyzed for determining the occurrence of pulse pile up. A number of known variations are possible to determine pulse pile up and some of these techniques can be extended to include correction using estimates formed from the sampled pulse. Energy analysis (i.e. windowing) analyzes the overall energy of a detected event and discards it if the event does not fall within pre-defined energy window(s). Energy analysis typically includes an assumption that event contamination will result in an apparent energy which is located outside of the pre-defined energy window(s).

Both of these approaches consume system data transmission bandwidth and computational resources in determining whether a detected event should be further processed for image generation or discarded. In addition, these methods for determining the validity of a detected event for image generation takes additional time for image data acquisition and/or image reconstruction. It is desirable to determine the usefulness of a detected event while reducing the consumption of system bandwidth and computational resources while still effectively selecting valid events for accurate images. It is further desirable to decrease the time required to select valid events to improve patient throughput and/or image generation. The present invention contemplates methods and apparatus that overcome the above-referenced problems and others.

In accordance with one aspect of the present invention, a method of accepting or rejecting a detected radiation event by an emission computed tomography (ECT) scanner prior to determining its location and/or integrated energy analysis is provided. The ECT scanner includes a matrix of sensors situated to view the event. The sensors have respective outputs that are responsive to the event. A method of filtering valid events from invalid events from a plurality of detected events includes acquiring a data stream of a plurality of detected events with a detector where a plurality of related signals is indicative of a single detected event. A correlation filter is applied to the data stream of a plurality of detected events to determine whether the detected events are valid. The correlation filter pattern based on a correlation of a plurality of signals resulting from a response of an associated detector to a plurality of single radiation events in an ideal dataset. The accepted data events are further processed into images.

A method of generating a filter for a nuclear medicine system is described wherein the filter sorts valid detected radiation events to be used for further image processing. The method includes providing a dataset indicative of a plurality of emitted radiation events occurring over a predetermined period of time. Signals are generated that are representative of the response of a detector to the dataset of the plurality of emitted radiation events. A pattern is determined based on a correlation of a plurality of signals resulting from the response of the detector to a plurality of single radiation events in the dataset. A filter is generated based on the correlation pattern.

In accordance with another aspect of the present invention, a gamma camera is provided for locating a radiation event in an emission computed tomography (ECT) scanner. The gamma camera includes an apparatus for filtering valid detected nuclear events from invalid events from a plurality of detected events. The apparatus includes a detector for acquiring a data stream of a plurality of detected events wherein a plurality of related signals is indicative of a single detected event. A processor applies a correlation filter to the data stream of a plurality of detected events to determine whether the detected events are valid. The correlation filter is a pattern based on a correlation between a plurality of signals resulting from a response of an associated detector to a plurality of single radiation events in an ideal dataset. A processor further processes the valid events into images.

One advantage of the present invention is the ability to improve image quality resulting from better spatial resolution and event positioning.

Another advantage of the present invention is the ability to reduce consumption of imaging system bandwidth and/or computation processor resources in determining the validity of a detected event.

Another advantage is improved patient throughput.

Yet another advantage is improved image processing time.

Still further advantages and benefits of the present invention will become apparent to those of ordinary skill in the art upon reading and understanding the following detailed description of the described embodiments applying principles of the present invention. An apparatus and method applying principles of the present invention provides the foregoing and other features hereinafter described and particularly pointed out in the claims. The following description and accompanying drawings set forth certain illustrative embodiments applying principles of the present invention. It is to be appreciated that different embodiments applying principles of the invention may take form in various components and arrangements of components. These described embodiments being indicative of but a few of the various ways in which the principles of the invention may be employed. The drawings are only for the purpose of illustrating such embodiments of an apparatus applying principles of the present invention and are not to be construed as limiting the invention.

Figure 1:
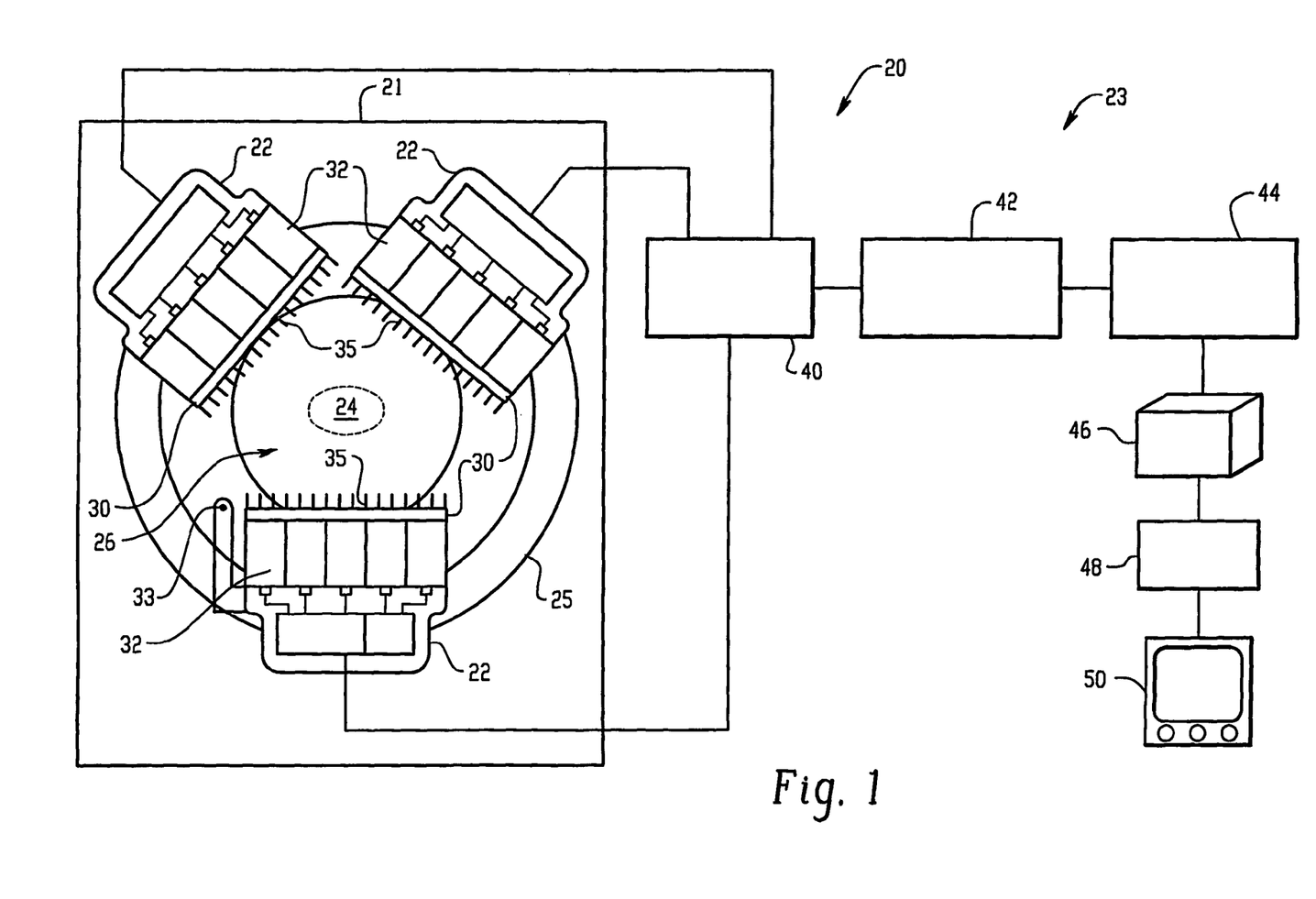
FIG. 1 is a diagrammatic illustration of an exemplary ECT scanner in accordance with aspects of the present invention.

With reference to FIG. 1, a nuclear ECT scanner 20 includes a gantry 21, a plurality of detector heads ("detectors") 22 facing and mounted for movement around a subject 24 (preferably containing a radionuclide distribution) and imaging system control console 23. The imaging system control console 23 coordinates the operation of the diagnostic imaging system 20. All of the control and imaging processing functions in the illustrated components and systems can be performed by known computer based systems having an operable complement of component systems such as suitable processors, memory and storage, input, output and data communications capabilities. In addition, portions of the functions may be distributed to one or more discrete processors within the system 20 that are in data communication with and provide appropriate signals to, the control console 23 for use in system operation and image generation.

Some of the functions of the system 20 applying principles of the present invention comprise a PMT signal correlation filter 40 in data communication with an event location and energy determination function 42. The filter 40 determines which signals from the detector 22 are provided to the location and energy function 42 for image processing. Next, a known reconstruction processor 44 receives the location and energy information to generate an image. The image is stored in an image memory 46 and subsequently provided to a video processor 48 to be processed for display on a monitor 50.

The subject 24 is located in an examination region 26. Each of the detectors 22 is mounted on a rotating gantry 25 and include a scintillator 30 that converts a radiation event (e.g., a ray of radiation from the radionuclide distribution that impinges on the scintillator 30) into a flash of light or scintillation. Optionally, a radiation source 33 produces a fan beam of transmission radiation of a different energy than the emission radiation from the radionucleide in the subject 24. Collimators 35 on the detectors 22 limit and define the paths or rays along which each detector 22 accepts emission and transmission radiation.

A matrix of sensors 32 is situated in each detector 22 to receive the light flashes from emitted radiation interacting with the scintillator 30. The matrix of sensors is a close hexagonal packed arrangement of PMTs. However, other sensors and packing arrangements are also contemplated. Alternatively, the scintillators and sensors may be distributed in a stationary manner around the examining region as is common in known Positron Emission Tomography (PET) scanners.

Each of the sensors 32 generates a respective output signal, e.g., an analog electrical pulse, in response to a received light flash, the output signal being proportional to that of the received light flash. In the case of an analog signal output, each of the sensors 32 is optionally electrically connected to analog-to-digital (A/D) converters that convert the respective analog outputs to digital signals. As is discussed in more detail below, the event location and energy function 42 measures or otherwise determines the location and/or energy of respective scintillation events that occur. The location of an event on the scintillator 30 is resolved and/or determined in a two dimensional (2D) Cartesian coordinate system with nominally termed x and y coordinates. However, other coordinate systems are contemplated.

Figure 2:
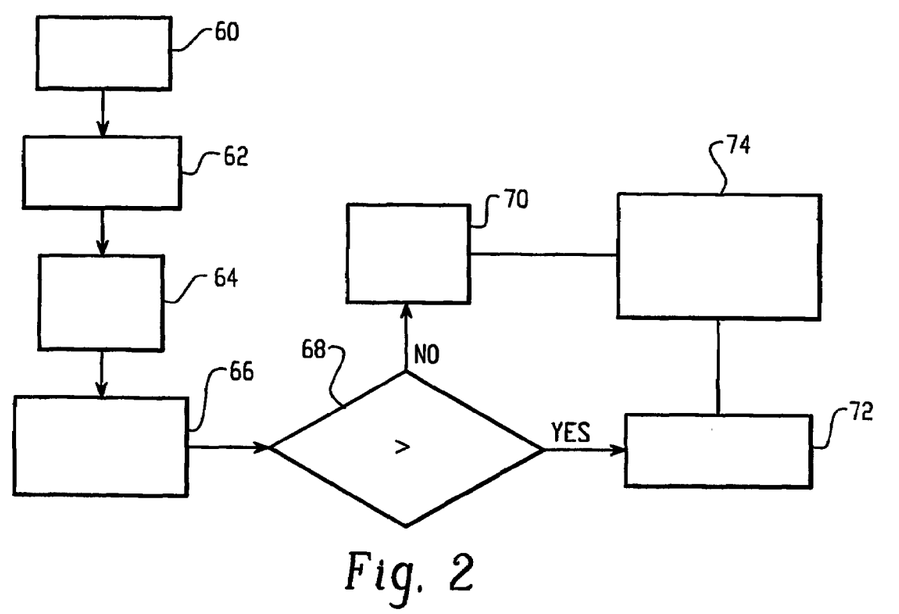
FIG. 2 is a flow chart showing an example of a method for generating a histogram in accordance with aspects of the present invention.

Turning now to FIG. 2, a method in accordance with principles of the present invention is further described. In step 60, a data set is collected for use in generating the PMT signal correlation filter histogram. One source for generating a dataset for the PMT signal correlation filter is to use empirical data as the basis for the correlation pattern. The data selected is representative of all data that are to be passed (i.e. not rejected by the filter). For example, a low count-rate point source has low pile-up and object scatter probability. Generally, data collected under these conditions are representative of 'ideal' data for a nuclear camera detector in an imaging system.

In addition to empirical data, analytic formulations based on idealized light distributions and detector response may also be used as the basis of the 'Ideal' data. In a similar manner, simulation of light response and/or detector response for a given configuration could also be used. In either case, a distribution of incident events is applied to the light response and detector response to form the data set. These alternate methods characterize response functions to generate a system and/or component response to the characteristic light distribution. In addition, the different methods for acquiring the dataset may be mixed, i.e. empiridcal response for the PMTs and analytical or simulated response for the scintillator or other components.

The distribution of incident events for either empirical, analytical or simulated solutions are used to define a data set of ideal emitted radiation events over a predetermined period of time for application with a detector. Alternatively, the spatial and/or energy distribution of the data set may be constrained. Restricting the energy distribution to events about the photo-peak, for example, would further prevent events that would otherwise have been rejected from effecting the correlation pattern.

The parameters of an ideal image data set established above are applied to collect (or generate in the case of analytic or simulation based parameters) the 'Ideal' data set. The data set has sufficient statistics to adequately represent the correlation pattern. For example, a suitable number of statistics is 100 counts received per element. If the entire volume containing the histogram for the correlation filter is 32768 voxels (elements), a suitable number of total counts for sufficient statistics is approximately 3,276,800 counts. This number of statistics is selected as reasonable for determining a suitable histogram signal correlation filter for clinical use and it is to be appreciated that a lesser numbers of counts would be acceptable for to generate a filter for lower levels of confidence in the effectiveness of the correlation filter to reject invalid events.

Next, in step 62, for each event the data values associated with the PMTs are normalized to the value of the PMT that is the maximum. Normalization eliminates energy dependence. Alternatively, as described in more detail below, the signals may be processed in accordance with principles of the present invention without normalization to the peak PMT.

Figure 3:
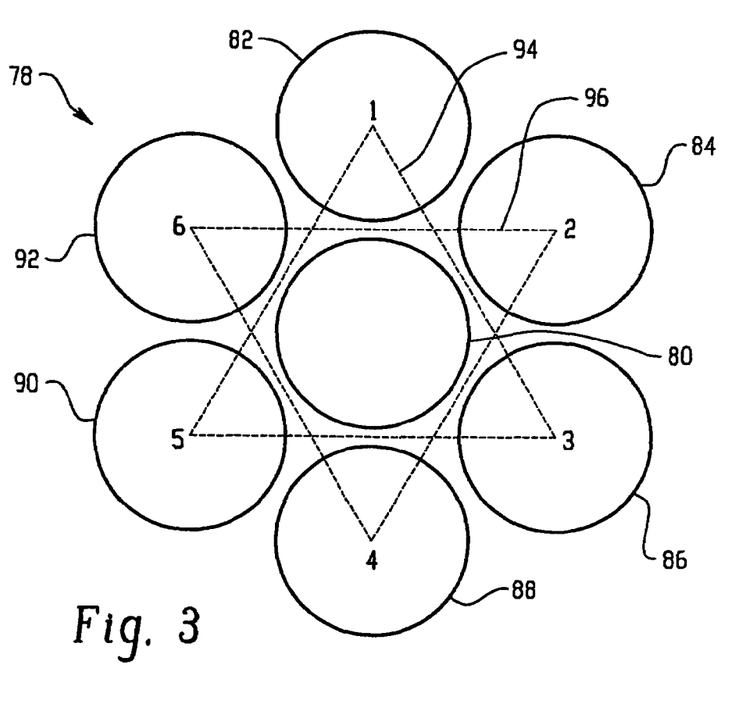
FIG. 3 is a diagrammatic illustration showing an exemplary arrangement and groupings of photomultiplier tubes in accordance with principles of the present invention.

In step 64, the data from each individual detected radiation event is used to select three (N=3) associated data values (a group). Referring to FIG. 3, the groups are identified and ordered by the specific physical relationship of the source PMTs located around the peak PMT. Two sub-sets, e.g. ordered triples, are formed out of an individual event since the physical relationships are symmetric and consistent. A typical PMT cluster 78 that responds to a single detected radiation event is shown. The peak PMT 80 is in the center of six associated source PMTs 82, 84, 86, 88, 90, and 92. The source PMTs 82-92 are arranged in two sub-sets (ordered triples) of three based on their spatial relationship. PMTs 82, 86 and 90 form one sub-set 94 and 84, 88 and 92 form another sub-set 96. The groups of associated data values in the index are selected such that a corresponding PMT from each sub-set 94, 96 (ordered triples) is included in each group. The value of N (number of groups) sets the number of dimensions, and therefore size, of the histogram that will be formed from the data. For example, referring to FIG. 4, a table 100 for generation of a volumetric histogram 102 in a three dimensional volume using three groups (N=3) is shown. The PMT signal values in the columns are associated with an axis of the histogram. Group 1 in column 1 includes PMTs 82 and 88 representing one axis 104 of the volume 102. Group 2 in column 2 includes PMTs 84, 90 corresponding to an axis 106 and group 3 in column 3 includes PMTs 86 and 92 corresponding to an axis 108. It is contemplated that the number of groups and/or elements included in the sub-sets may be varied.

The grouping of PMTs for a single event provides a means to increase the statistics for generation of the correlation filter. Single PMT values as well as alternate pairings or groups may be identified and stored in a column associated with an axis of the histogram. In addition, the individual values or ordered groups may be representative of PMT signal value relationships as well as spatial relationships. For example, the values stored in the columns may consist of the maximum value of the source PMTs after normalization and the values from the two opposing PMTs (a combination of value and spatial relationships). For a given light distribution, detector response and incident event distribution, the group is selected to create a strongly defined correlation pattern. Selection of groups that result in slowly changing, broad correlation patterns provide less filtering and therefore less event discrimination for selection of valid events for image generation.

In step 66, for each event the values of the ordered groups in the event data form an index (rows in table 100) for a three (N=3) dimensional space. Each dimension (axis of the volume) is represented by a column as described above. Each time a given index having specific values in each of the columns is formed, a counter (column 4) associated with that index (row) is incremented. For example, turning to the table in FIG. 4, the peak PMT value Max P is set as 0.5 (if any other PMT had a value greater than 0.5, it would be the peak PMT). The values for the source PMTs 82-92 range from 0 to 0.5. By way of an example, a specific single radiation event from the data set can result in PMT 82 or 88 (No's 1 and 4 in column 1) providing signals for storage in column 1 having a value of 0.2 individually. It is also contemplated that the individual PMT signals may be combined. Likewise PMTs 84 or 90 in column 2 may result in a value of 0.2 being stored in column 2 and PMTs 86 or 92 can result in a value of 0.1 being stored in column 3. The corresponding index of $H_{(0.2),(0.2)(0.1)}$ shown in row 110 is indexed with one count. In the volume 102, shown in FIG. 4, this set of values corresponds to $H_{X,Y,Z}$ and an element (voxel) position within the volume at {0.2,0.2,0.1} Referring to column 4, a listing is illustrated for combinations for particular indexes.

Figure 4A:
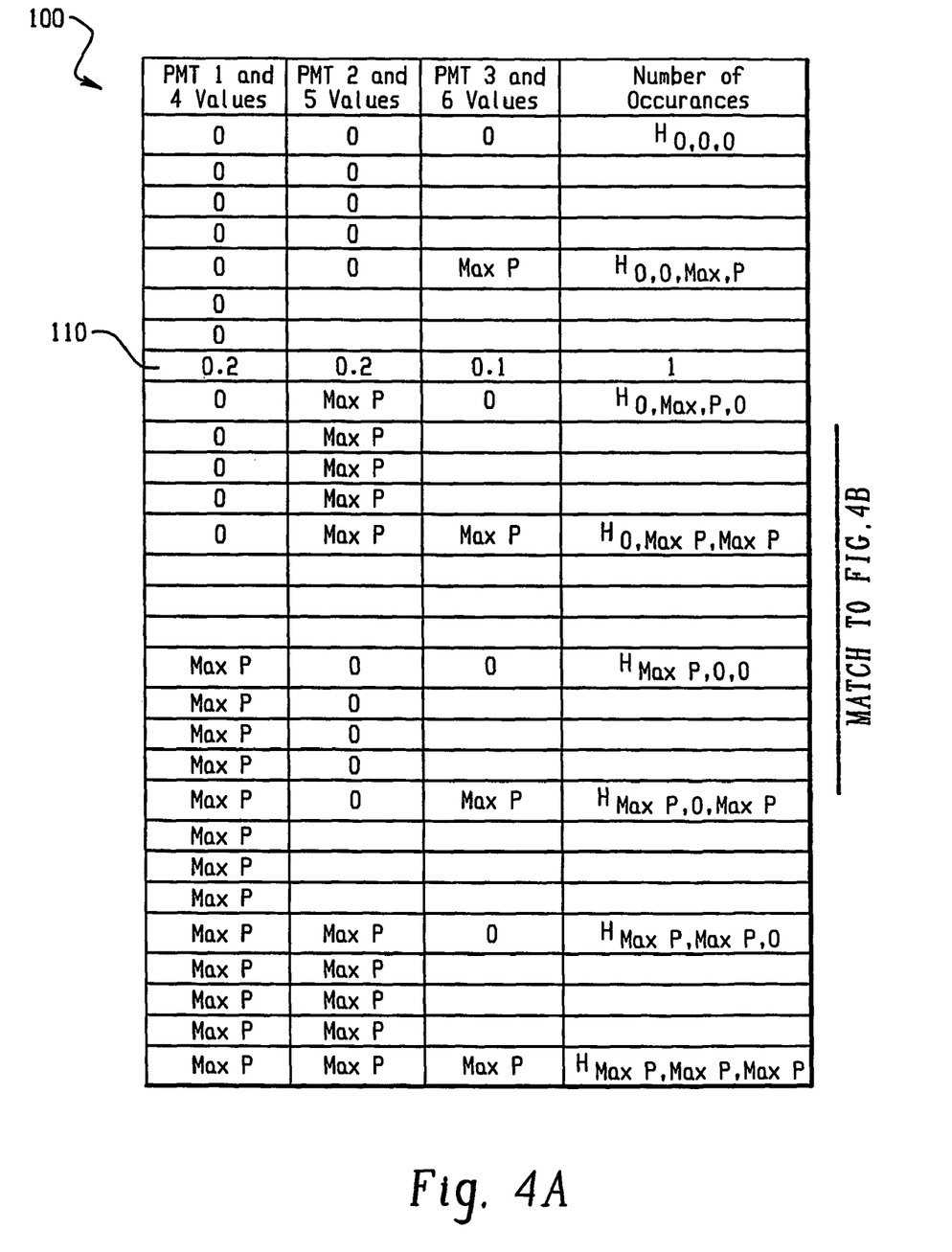
FIG. 4 is an illustration of an index of event data for a histogram in accordance with principles of the present invention.
Figure 4B:
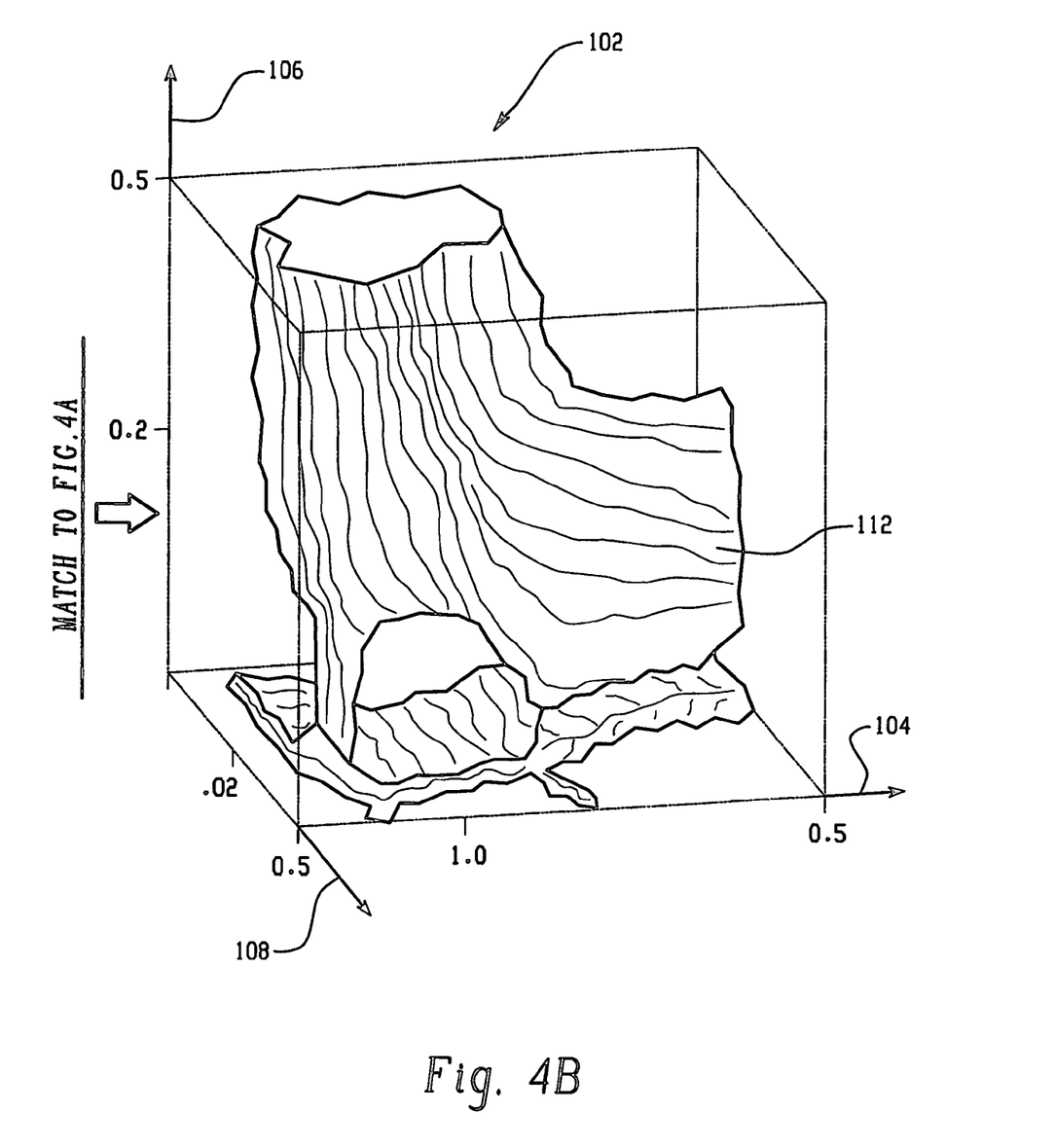

In this way, an N dimensional histogram is formed. In the described example, the N=3 the histogram fills a three dimensional volume. It is to be appreciated that other values of N may be selected. If the events of the data set represent an 'Ideal' data set, then the volume 102 marks the boundary of valid and invalid ordered groupings of event data.

The histogram formed in step 66 is the correlation pattern for use in the PMT signal correlation filter. For the histogram to be useful, however, the histogram elements must be converted from continuous values to a simple 'pass' or 'reject' flag. In step 68 a threshold is applied to the histogram elements to perform this conversion. Elements within the three dimensional volume that exceeded the threshold number of occurrences are marked as 'Pass' elements. Within the volume 102 is a filled in portion 112, where a sufficient number of events occurred that were counted in column 4. The threshold is selected based on the data set used as the 'Ideal' data set. Since event inter-arrival time probabilities generally do not drop to 0, pile-up, for example, can occur at any count-rate. This and other non-ideal effects will be present in any empirical data set. As a result, outliers will be present. The threshold is selected so as to strongly define the pattern and remove these outliers. For example, the threshold may be set at 100 counts before an indexed set of values are included in the filled in area 112 of the volume 102. Where the volume 102 is empty, an insufficient number of events occurred.

If the determination in step 68 is negative, the data set did not provide enough counts for the given index (row), the process proceeds to step 70 where the element in the volume is marked as a reject element. If the determination in step 68 is affirmative, the element in the volume 102 is marked as a pass element. In step 74, The process then stores the results of the determination of step 68 and element marking of steps 70, 72.

Figure 5:
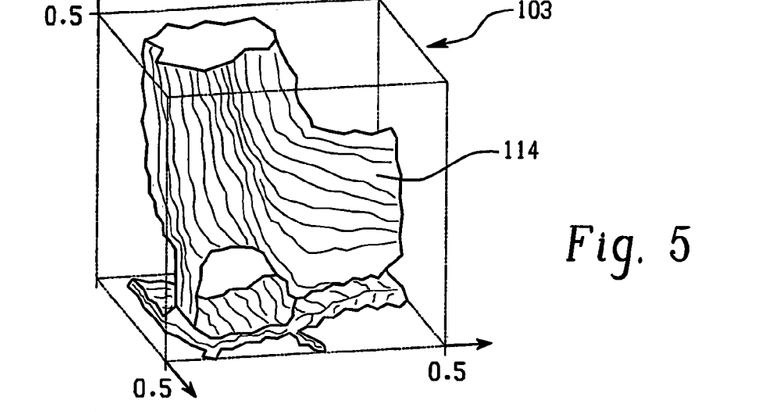
FIG. 5 is an illustration of an example of a correlation filter volume in accordance with principles of the present invention.
Figure 6:
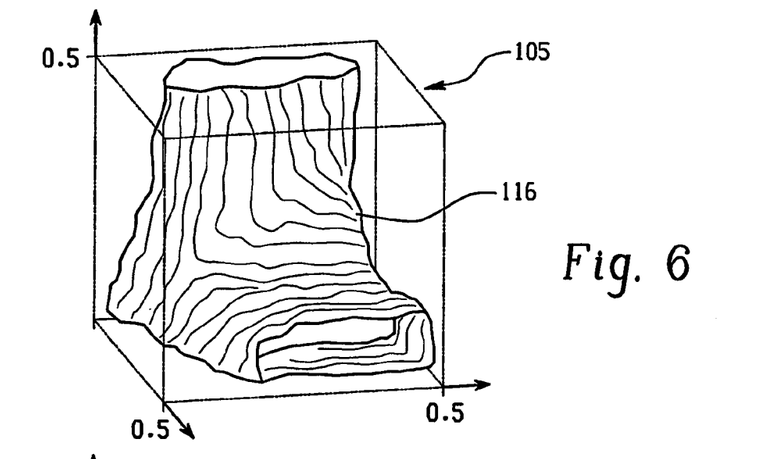
FIG. 6 is an illustration of another example of a correlation filter volume in accordance with principles of the present invention.
Figure 7:
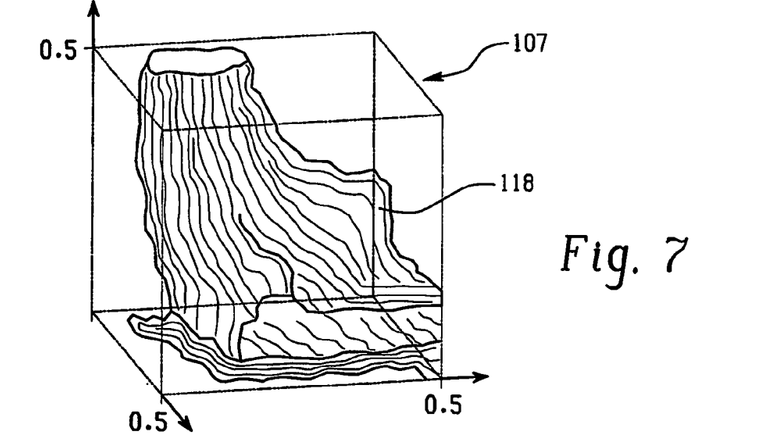
FIG. 7 is an illustration of another example of a correlation filter volume in accordance with principles of the present invention.

Referring to FIGS. 3, 5, 6, and 7, some examples of histograms having different PMT pairings and axis relationships are illustrated. In FIG. 5, the volume 103 represents ordered triples {X,Y,Z} corresponding to the PMT cluster subsets 94, 96 in FIG. 3 of {82,86,90} and {84,88,92}. This corresponds to storing values from PMTs 82, 84 in column 1 of the table, PMTs 86, 88 in column 2 and PMTs 90, 92 in column 3. The pass events are represented by the pattern of a filled in area 114. FIG. 6 illustrates ordered triples of {82,84,86} and {88,90,92} corresponding to a volume 105 and a filter pattern area of 116. FIG. 7 illustrates ordered triples of {82, 84, 90} and {86, 88, 92} corresponding to a volume 107 and a filter pattern area of 118.

When one of the patterns of the filled in areas 112, 114, 116, 118 is applied to a subsequent event data stream from PMTs during an imaging scan, the ordered groups of data from a given event will be filtered according to the pattern. A method of applying the histogram of the present invention applies the PMT signal correlation filter 40 to the detected event data stream and selects whether to pass or reject the event prior to consuming substantial system bandwidth and computation resources.

Alternatively, the PMT signals are processed to generate the histogram without normalization of source PMTs 82-92 to the peak PMT 80. For example, consider the ordered triple {X, Y, Z} that occurred when energy is E. When energy goes up by n to nE, the triple becomes {nX, nY, nZ}. Without normalization, {X, Y, Z} and {nX, nY, nZ} map to two different voxels. With normalization, as described in the embodiment above, they both map to {X/E, Y/E, Z/E}. So, although all the events could have been at the same spatial location, if they occur over a varying energy distribution, non-normalized, they will map to a series of voxels or elements within the histogram volume. When the PMT values are normalized, they map to 1 voxel or element of the histogram volume.

In general, the statistics for the non-normalized embodiment result in the pattern getting more spread out (i.e. need more events in an 'ideal' data set for the sufficient number of counts for valid statistics). Also, if the apparent energy drifts (due to temperature effects for example) between the 'ideal' data and the data to be filtered, the pattern density changes and threshold selection becomes more important. On the other hand, when using the non-normalized values to generate the histogram, energy is folded into the correlation. For example, light collection (and therefore energy) changes spatially. Those changes are reflected in the density of the correlation pattern and filter. Application of a threshold based on a non-normalized histogram filters out events as a result of the specific combination of energy and spatial location.

Figure 8:
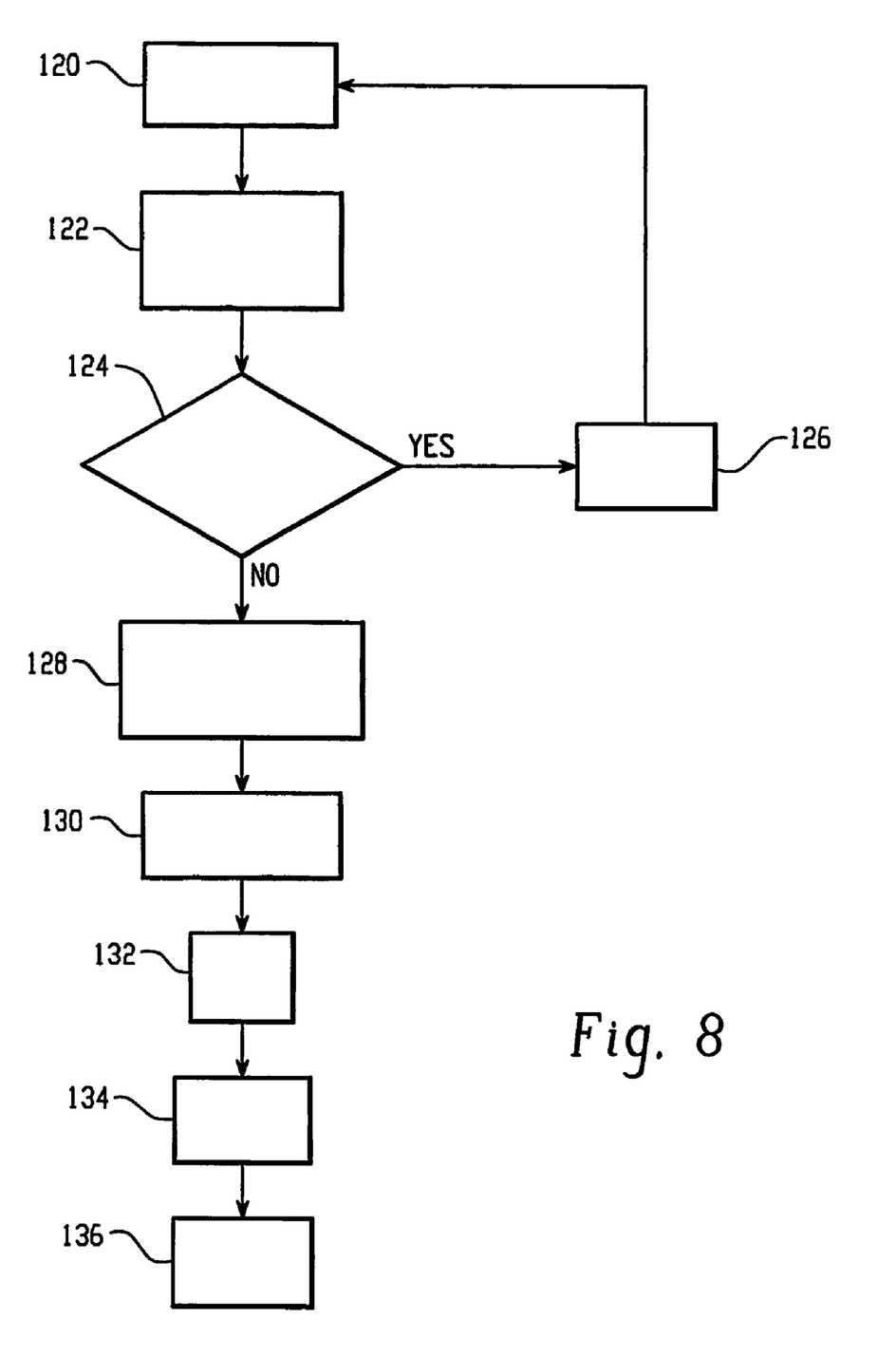
FIG. 8 is a flow chart showing an example of a method of applying principles of the present invention.

Turning now to FIG. 8, a method is shown illustrating application of the PMT correlation filter according to principles of the present invention. In step 120, PMT signals are acquired when an emitted radiation event is detected from a subject 24 and converted into sensor output signals, which are transmitted to a processor in data communication with the control consul 23. The processor may be located in the detector head 22 or other suitable location within the system. The processor contains the PMT signal correlation filter 40 and detects that an event occurs. The processor identifies and/or selects sensor outputs that will be used, prepared and/or sampled to be applied to the PMT signal correlation filter 40. For example, signals are selected from source PMTs 82-92 to be applied to the signal correlation filter 40.

In step 122, the PMT signal correlation filter 40, represented by the histograms in FIGS. 4-7, is applied to the PMT signal data stream from a detector 22 representative of a detected event. The ordered groups of data from a given event will index into the pattern of elements of the PMT signal correlation filter 40. In step 124 a determination is made as to whether the pattern of received PMT signals indexes to one of the pass classified areas within the filled in volume 112 of a histogram. If the determination is negative, that the event is contaminated and corresponds to a reject element in the histogram, the event data is classified as a discard event in step 126 and the process returns to step 120 making system resources available to process another detected event in the detector data stream. If the indexed pattern is determined to index to a pass element of the histogram, i.e. within the filled in volume 112, the event is passed to step 128 for further processing as a valid detected event.

In step 128, the location and energy of the detected event are determined using known methods. The location of a resulting scintillation and the position of the receiving detector 22 uniquely determine the detected ray such that the control console 23 determines the energy and the location of each scintillation on the face of the detectors 22, hence the ray along which the radiation originated. For PET scanning, suitable coincidence determinations and other known processes provide the location of the detected event. Once the positions and energies are determined at which scintillations occurred, the process continues to step 130 where the reconstruction processor 44 reconstructs an image representation from the emission data. When the radiation source 33 is used, transmission data (similarly identified via the energy associated with the data) is used to correct the emission data for an improved image, e.g., by generating an attenuation map of the subject 24.

Next, in step 132, the image representation is stored in the image memory 46. In step 134, the video processor 48 retrieves the stored image and processes the image representation data for display on the monitor 50.

While a particular feature of the invention may have been described above with respect to a particular the illustrated embodiment, such features may be combined with one or more other features of other embodiments, as may be desired and advantageous for any given particular application.

From the above description of the invention, those skilled in the art will perceive improvements, changes and modification. Such improvements, changes and modification within the skill of the art are intended to be covered by the appended claims.

The invention claimed is:

1. A method of generating a filter for a nuclear medicine imaging system, the filter for selecting valid detected radiation events for image processing, the method comprising:
  providing a dataset indicative of a plurality of emitted radiation events occurring over a predetermined period of time;
  generating signals representative of the response of a detector to the dataset of the plurality of emitted radiation events;
  determining a correlation pattern based on a correlation of a plurality of signals resulting from the response of the detector for each of a plurality of single radiation events in the dataset;
  generating a filter based on the correlation pattern; and
  storing the generated filter as a histogram.

2. The method of claim 1 wherein the histogram is three dimensional.

3. The method of claim 1 wherein the data set is obtained by at least one of empirical acquisition, analytical generation and simulation.

4. The method of claim 1 wherein determining a pattern includes indexing the response of the detector to a single radiation event.

5. The method of claim 4 wherein generating the filter includes comparing the number of occurrences of the indexed response of the detector to single radiation events to a threshold value.

6. The method of claim 5 wherein the threshold value is a predetermined number of occurrences of the indexed response over a predetermined period of time.

7. A method of generating a filter for a nuclear medicine imaging system, the filter for selecting valid detected radiation events for imaging processing, the method comprising:
  providing a dataset indicative of a plural of emitted radiation events occurring over a predetermined period of time;
  generating signals representative of the response of a detector to the dataset of the plurality of emitted radiation events;
  determining a correlation pattern based on a correlation of a plurality of signals resulting from the response of the detector for each of a plurality of signals radiation events in the dataset; and
  generating a filter based on the correlation pattern; wherein the correlation pattern is determined from signals based on at least one photomultiplier tube sub-set near a peak photomultiplier tube.

8. The method of claim 7 wherein the at least one sub-set is an ordered triple.

9. The method of claim 8 wherein the at least one subset is selected based on spatial relationship and each element in the at least one subset corresponds to a dimension in the filter.

10. The method of claim 7 wherein each of the individual signals of the sub-set correspond to a dimension in a histogram representative of the correlation pattern filter.

11. The method of claim 7 wherein the signals representative of the at least one photomultiplier sub-set are normalized to the peak photomultiplier tube signal.

12. A method of filtering valid events from invalid events from a plurality of detected events, the method comprising:
  acquiring a data stream of a plurality of detected events with a detector wherein a plurality of related signals is indicative of a single detected event;
  applying a correlation filter to the data stream of a plurality of detected events to determine whether the detected events are valid, the correlation filter generating a pattern based on a correlation of a plurality of signals resulting from a response of an associated detector to a plurality of single radiation events in an ideal dataset; and
  processing the valid events; and
  determining the location of the detected event after applying the correlation filter to the detected events.

13. The method of claim 12 wherein the correlation filter is determined from signals based on at least one photomultiplier tube sub-set near a peak photomultiplier tube.

14. The method of claim 13 wherein the at least one sub-set is an ordered triple.

15. The method of claim 13 wherein each of the PMT signals of the acquired data stream of detected events of the sub-set correspond to a dimension in a histogram representative of the correlation filter.

16. The method of claim 15 wherein the at least one sub-set is selected based on spatial relationship.

17. The apparatus of claim 13 wherein the correlation filter is applied to a plurality of signals from at least one photomultiplier tube sub-set near a peak photomultiplier tube.

18. The apparatus of claim 17 including means for arranging the at least one sub-set of signals in an ordered triple.

19. The apparatus of claim 17 including means to arrange each of the individual photomultiplier tube values of the at least one photomultiplier tube sub-set of the acquired data stream of detected events to correspond to an associated dimension in a histogram applied as the correlation filter.

20. A method of filtering valid events from invalid events from a plurality of detected events, the method comprising:
  acquiring a data stream of a plurality of detected events with a detector wherein a plurality of related signals is indicative of a single detected event;
  applying a correlation filter to the data stream of a plurality of detected events to determine whether the detected events are valid, the correlation filter generating a pattern based on a correlation of a plurality of signals resulting from a response of an associated detector to a plurality of single radiation events in an ideal dataset;
  processing the valid events;
  wherein the correlation filter includes a histogram.

21. The method of claim 20 wherein the histogram is three dimensional.

22. An apparatus for filtering valid detected nuclear events from invalid events from a plurality of detected events, the apparatus comprising:

a detector for acquiring a data stream of a plurality of detected events wherein a plurality of related signals is indicative of a single detected event;

a processor for applying a correlation filter to the data stream of a plurality of detected events to determine whether the detected events are valid, the correlation filter generating a pattern based on a correlation of a plurality of signals resulting from a response of an associated detector to a plurality of single radiation events in an ideal dataset;

a processor for processing the valid events into images; and means for determining the location of the detected event after applying the correlation filter to the detected events.

23. An apparatus for filtering valid detected nuclear events from invalid events from a plurality of detected events, the apparatus comprising:

a detector for acquiring a data stream of a plurality of detected events wherein a plurality of related signals is indicative of a signal detected event;

a processor for applying a correlation filter to the data stream of a plurality of detected events to determine whether the detected events are valid, the correlation filter generating a pattern based on a correlation of a plurality of signals resulting from a response of an associated detector to a plurality of signal radiation events in an ideal dataset; and a processor for processing the valid events into images;

wherein the correlation filter includes a histogram.

24. The apparatus of claim 23 wherein the histogram is three dimensional.

* * * * *